United States Patent
Su et al.

(10) Patent No.: US 9,062,011 B2
(45) Date of Patent: Jun. 23, 2015

(54) BENZOXAZINE INTERMEDIATE AND PREPARATION METHOD THEREOF

(75) Inventors: Shiguo Su, Guangdong (CN); Yueshan He, Guangdong (CN)

(73) Assignee: Shengyi Technology Co., Ltd., Guangdong (CN)

( * ) Notice: Subject to any disclaimer, the term of this patent is extended or adjusted under 35 U.S.C. 154(b) by 0 days.

(21) Appl. No.: 14/235,374

(22) PCT Filed: Oct. 18, 2011

(86) PCT No.: PCT/CN2011/080950
§ 371 (c)(1),
(2), (4) Date: Jan. 27, 2014

(87) PCT Pub. No.: WO2013/056428
PCT Pub. Date: Apr. 25, 2013

(65) Prior Publication Data
US 2014/0206864 A1    Jul. 24, 2014

(51) Int. Cl.
*C07D 265/12*      (2006.01)
(52) U.S. Cl.
CPC .................................. *C07D 265/12* (2013.01)
(58) Field of Classification Search
CPC ................................................... C07D 265/12
USPC ........................................................... 544/89
See application file for complete search history.

(56) References Cited

U.S. PATENT DOCUMENTS

2009/0240006 A1    9/2009  Ishida et al.

FOREIGN PATENT DOCUMENTS

| CN | 1900068 A | 1/2007 |
|---|---|---|
| CN | 101235131 A | 8/2008 |
| CN | 102516194 A | 6/2012 |

*Primary Examiner* — Kahsay Habte
(74) *Attorney, Agent, or Firm* — McDonald Hopkins LLC

(57) ABSTRACT

The present invention relates to a benzoxazine intermediate and a preparation method thereof. The structural formula of the benzoxazine intermediate is shown by formula (1), $R_1$ in formula represents O, C=O, S, $SO_2$, alicyclic hydrocarbon with 3 to 30 carbon atoms and derivatives thereof, aliphatic hydrocarbon with 1 to 20 carbon atoms and derivatives thereof, or unsaturated aliphatic hydrocarbon with 2 to 20 carbon atoms and derivatives thereof; $R_2$ is alicyclic hydrocarbon with 3 to 20 carbon atoms and derivatives thereof, aliphatic hydrocarbon with 1 to 20 carbon atoms and derivatives thereof, or unsaturated aliphatic hydrocarbon with 2 to 20 carbon atoms and derivatives thereof. The benzoxazine intermediate of the present invention contains a naphthalene ring structure segment, has desirable heat resistance performance and flame retarding performance, and can be widely applied in composite materials.

9 Claims, No Drawings

BENZOXAZINE INTERMEDIATE AND PREPARATION METHOD THEREOF

TECHNICAL FIELD

The present invention relates to a benzoxazine intermediate, especially a benzoxazine intermediate and a preparation method thereof.

BACKGROUND ART

On the basis of the conventional method for preparing a phenolic resin, a cyclization reaction of primary amines, phenols and aldehydes is carried out to obtain a benzoxazine intermediate. Under the heating or catalyst conditions, a ring-opening reaction of benzoxazine is carried out to produce a novel thermosetting resin having a net structure, wherein the condensate has a better heat resistance, fire resistance and electricity property.

Among the raw materials for preparing benzoxazine intermediate, the aldehydes used therein include formalin, paraformaldehyde; the amines include aromatic amines, alkyl primary amines, alicyclic primary amines; the phenols are primarily single phenol compounds, bisphenol compounds, trisphenol compounds, multifunctional phenols, phenolic resins, para hydroxystyrene, polymers or copolymers thereof. However, there is no report that the phenol as shown in Formula (2) is used as the phenol source for preparing a benzoxazine intermediate.

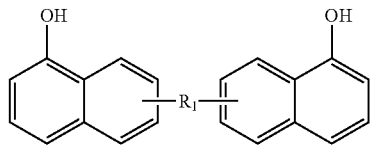

CONTENTS OF THE INVENTION

The object of the present invention lies in providing a benzoxazine intermediate, which contains a naphthalene ring structure segment, has desirable heat resistance performance and flame retarding performance and can be widely applied in composite materials.

Another object of the present invention lies in providing a method for preparing a benzoxazine intermediate, which uses the compound of the formula (2) as the phenol source and involves preparing together with primary amine and aldehyde a benzoxazine intermediate containing the structure of the formula (2). The method is simple and easy to operate.

In order to achieve said objects, the present invention provides a benzoxazine intermediate having the following structural formula (I):

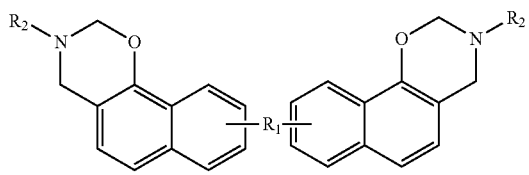

wherein $R_1$ is selected from the group consisting of O, C=O, S, $SO_2$, alicyclic hydrocarbon with 3 to 20 carbon atoms and derivatives thereof, aliphatic hydrocarbon with 1 to 20 carbon atoms and derivatives thereof, or unsaturated aliphatic hydrocarbon with 2 to 20 carbon atoms and derivatives thereof; $R_2$ is selected from the group consisting of alicyclic hydrocarbon with 3 to 20 carbon atoms and derivatives thereof, aliphatic hydrocarbon with 1 to 20 carbon atoms and derivatives thereof, or unsaturated aliphatic hydrocarbon with 2 to 20 carbon atoms and derivatives thereof.

Meanwhile, the present invention provides a method for preparing a benzoxazine intermediate, comprising the following steps:

Step 1: quantifying the phenol, primary amine and aldehyde according to the molar ratio of phenolic hydroxyl group:amine group:aldehyde group of 1:(0.8-1.2):(1.5-2.5); the catalyst is added in an amount of 0.1-5 wt. % relative to the total amount;

Step 2: mixing the phenol, primary amine and aldehyde, adding a catalyst to adjust the pH thereof to 8-10, and ending the reaction after the heating and reflux reaction for 1-8 h;

Step 3: washing with deionized water, condensing, purifying and drying the resultant solution to obtain a benzoxazine intermediate having the structural formula (I)

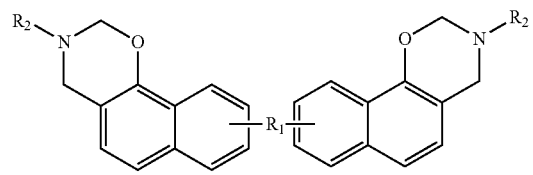

wherein $R_1$ is selected from the group consisting of O, C=O, S, $SO_2$, alicyclic hydrocarbon with 3 to 20 carbon atoms and derivatives thereof, aliphatic hydrocarbon with 1 to 20 carbon atoms and derivatives thereof, or unsaturated aliphatic hydrocarbon with 2 to 20 carbon atoms and derivatives thereof; $R_2$ is selected from the group consisting of alicyclic hydrocarbon with 3 to 20 carbon atoms and derivatives thereof, aliphatic hydrocarbon with 1 to 20 carbon atoms and derivatives thereof, or unsaturated aliphatic hydrocarbon with 2 to 20 carbon atoms and derivatives thereof.

The catalyst is added in an amount of 0.1-5 wt. % relative to the total amount.

The phenol has the following structural formula (2)

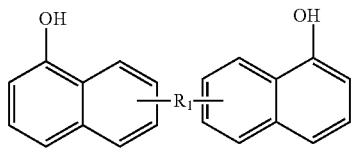

wherein $R_1$ is selected from the group consisting of alicyclic hydrocarbon with 3 to 20 carbon atoms and derivatives thereof, aliphatic hydrocarbon with 1 to 20 carbon atoms and derivatives thereof, or unsaturated aliphatic hydrocarbon with 2 to 20 carbon atoms and derivatives thereof.

The primary amine is $NH_2R_2$ in which $R_2$ is selected from the group consisting of alicyclic hydrocarbon with 3 to 20 carbon atoms and derivatives thereof, aliphatic hydrocarbon with 1 to 20 carbon atoms and derivatives thereof, or unsaturated aliphatic hydrocarbon with 2 to 20 carbon atoms and derivatives thereof.

The primary amine is selected from the group consisting of allyl amine, aniline, cyclopropylamine methylamine and ethylamine.

The aldehyde is an aqueous formaldehyde solution or paraformaldehyde.

The catalyst is selected from the group consisting of KOH solution, NaOH solution, ammonia, triethanolamine and triethylamine.

The benzoxazine intermediate is prepared by the solution synthesis method or melt synthesis method, wherein, when the solution synthesis method is used, phenol, primary amine and aldehyde are added in step 2 into the solvent, heated and refluxed; the solvent is selected from the group consisting of toluene, xylene, ethanol, acetone, butanone, methylisobutanone, ethylene glycol monomethyl ether, ethylene glycol ether, ethylene glycol methyl ether acetate, methylformamide and tetrahydrofuran, or mutual compounds thereof.

The present invention has the following beneficial effects. The benzoxazine intermediate of the present invention is prepared by using the phenol of the formula (2) as the phenol source together with primary amine and aldehyde. The benzoxazine intermediate contains a naphthalene ring structure segment, has desirable heat resistance performance and flame retarding performance and can be widely applied in composite materials. The preparation method thereof is simple and easy to operate.

EMBODIMENTS

The present invention provides a benzoxazine intermediate having the following structural formula (I):

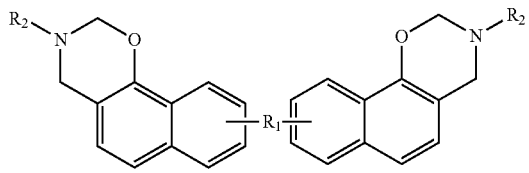

wherein $R_1$ is selected from the group consisting of O, C=O, S, $SO_2$, alicyclic hydrocarbon with 3 to 20 carbon atoms and derivatives thereof, aliphatic hydrocarbon with 1 to 20 carbon atoms and derivatives thereof, or unsaturated aliphatic hydrocarbon with 2 to 20 carbon atoms and derivatives thereof; $R_2$ is selected from the group consisting of alicyclic hydrocarbon with 3 to 20 carbon atoms and derivatives thereof, aliphatic hydrocarbon with 1 to 20 carbon atoms and derivatives thereof, or unsaturated aliphatic hydrocarbon with 2 to 20 carbon atoms and derivatives thereof.

One example of the method for preparing a benzoxazine intermediate involves using the solution synthesis method comprising the following steps:

Step 1: quantifying the phenol, primary amine and aldehyde according to the molar ratio of phenolic hydroxyl group:amine group:aldehyde group of 1:(0.8-1.2):(1.5-2.5); the phenol has the following structural formula (2)

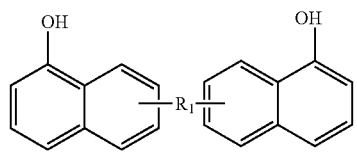

wherein $R_1$ is selected from the group consisting of O, C=O, S, $SO_2$, alicyclic hydrocarbon with 3 to 20 carbon atoms and derivatives thereof, aliphatic hydrocarbon with 1 to 20 carbon atoms and derivatives thereof, or unsaturated aliphatic hydrocarbon with 2 to 20 carbon atoms and derivatives thereof. The primary amine is $NH_2R_2$ in which $R_2$ is selected from the group consisting of alicyclic hydrocarbon with 3 to 20 carbon atoms and derivatives thereof, aliphatic hydrocarbon with 1 to 20 carbon atoms and derivatives thereof, or unsaturated aliphatic hydrocarbon with 2 to 20 carbon atoms and derivatives thereof. The primary amine is selected from the group consisting of allyl amine, aniline, cyclopropylamine methylamine and ethylamine. The aldehyde is formalin or paraformaldehyde.

Step 2: adding phenol, primary amine and aldehyde into the solvent, adding a catalyst to adjust the pH thereof to 8-10, wherein the catalyst is added in an amount of 0.1-5 wt. % relative to the total amount, and ending the reaction after the heating and reflux reaction for 1-8 h. The catalyst is selected from the group consisting of KOH solution, NaOH solution, ammonia, triethanolamine and triethylamine. The solvent is selected from the group consisting of toluene, xylene, ethanol, acetone, butanone, methylisobutanone, ethylene glycol monomethyl ether, ethylene glycol ether, ethylene glycol methyl ether acetate, methylformamide and tetrahydrofuran, or mutual compounds thereof.

Step 3: washing with deionized water, condensing the resultant solution, removing the residual solvent, purifying and drying to obtain a benzoxazine intermediate.

Another example of the method for preparing a benzoxazine intermediate involves using the solvent-free melt synthesis method comprising the following steps:

Step 1: quantifying the phenol, primary amine and aldehyde according to the molar ratio of phenolic hydroxyl group:amine group:aldehyde group of 1:(0.8-1.2):(1.5-2.5); the phenol has the following structural formula (2)

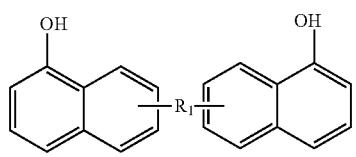

wherein R1 is selected from the group consisting of O, C=O, S, SO2, alicyclic hydrocarbon with 3 to 20 carbon atoms and derivatives thereof, aliphatic hydrocarbon with 1 to 20 carbon atoms and derivatives thereof, or unsaturated aliphatic hydrocarbon with 2 to 20 carbon atoms and derivatives thereof. The primary amine is $NH_2R_2$ in which $R_2$ is selected from the group consisting of alicyclic hydrocarbon with 3 to 20 carbon atoms and derivatives thereof, aliphatic hydrocarbon with 1 to 20 carbon atoms and derivatives thereof, or unsaturated aliphatic hydrocarbon with 2 to 20 carbon atoms and derivatives thereof. The primary amine is selected from the group consisting of allyl amine, aniline, cyclopropylamine methylamine and ethylamine. The aldehyde is formalin or paraformaldehyde.

Step 2: mixing phenol, primary amine and aldehyde together, adding a catalyst to adjust the pH thereof to 8-10, wherein the catalyst is added in an amount of 0.1-5 wt. % relative to the total amount, and ending the reaction after the heating and reflux reaction for 1-8 h. The catalyst is selected from the group consisting of KOH solution, NaOH solution, ammonia, triethanolamine and triethylamine.

Step 3: washing with deionized water, condensing the resultant solution, purifying and drying to obtain a benzoxazine intermediate.

The present invention is explained with the examples as follows, but not limited within the scope of the examples.

Example 1

Preparation of Benzoxazine Intermediate by the Solution Synthesis Method

At room temperature, phenol was dissolved in anhydrous ethanol; the pH was adjusted to 8-10; toluene, aniline and formalin were added according to the molar ratio of phenolic hydroxyl group:amine group:aldehyde group of 1:1:2. After being homogeneously stirred, the mixture was heated and refluxed, reacted for 4 h to vacuum distill off ethanol, water, toluene, and placed in a cooling unit. Butanone was added to obtain a yellowish, translucent viscous body. The viscous body was washed, purified and dried to obtain a benzoxazine intermediate having the following structural formula, wherein the yield is 80.5%.

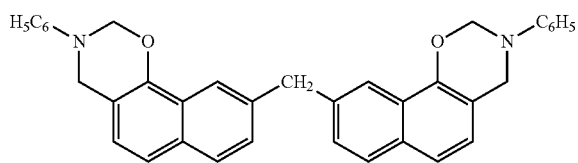

Example 2

Preparation of Benzoxazine Intermediate by the Solution Synthesis Method

At room temperature, phenol was dissolved in anhydrous ethanol; the pH was adjusted to 8-10; toluene, aniline and paraformaldehyde were added according to the molar ratio of phenolic hydroxyl group:amine group:aldehyde group of 1:1.2:2.5. After being homogeneously stirred, the mixture was heated and refluxed, reacted for 4 h to vacuum distill off ethanol, water, toluene, and placed in a cooling unit. Butanone was added to obtain a yellowish, translucent viscous body. The viscous body was washed, purified and dried to obtain a benzoxazine intermediate having the following structural formula, wherein the yield is 78.8%.

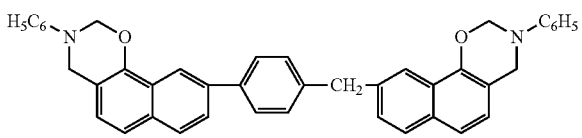

Example 3

Preparation of Benzoxazine Intermediate by the Solution Synthesis Method

At room temperature, phenol was dissolved in anhydrous ethanol; the pH was adjusted to 8-10; toluene, allyl amine and paraformaldehyde were added according to the molar ratio of phenolic hydroxyl group:amine group:aldehyde group of 1:0.8:1.5. After being homogeneously stirred, the mixture was heated and refluxed, reacted for 4 h to vacuum distill off ethanol, toluene, and placed in a cooling unit. Butanone was added to obtain a yellowish, translucent viscous body. The viscous body was washed, purified and dried to obtain a benzoxazine intermediate having the following structural formula, wherein the yield is 75.5%.

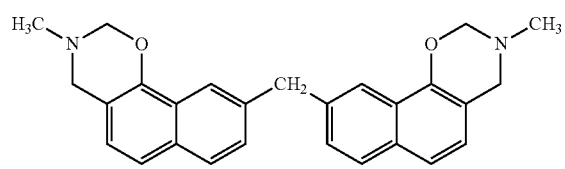

Example 4

Preparation of Benzoxazine Intermediate by the Melt Synthesis Method

At room temperature, phenol, allyl amine and paraformaldehyde were added according to the molar ratio of phenolic hydroxyl group:amine group:aldehyde group of 1:1:2. After being homogeneously stirred, the mixture was heated to a molten state, reacted for 4 h and placed in a cooling unit to obtain a yellowish, translucent viscous body. The viscous body was washed, purified and dried to obtain a benzoxazine intermediate having the following structural formula, wherein the yield is 82.1%.

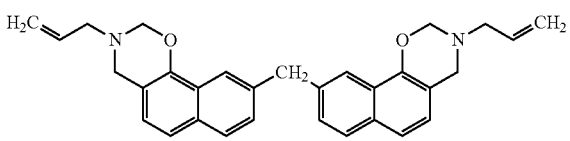 [SMILES: C=CCN1COc2c(ccc3ccc(Cc4ccc5ccc6c(c5c4)OCN(CC=C)C6)cc23)C1]

Example 5

Preparation of Benzoxazine Intermediate by the Melt Synthesis Method

At room temperature, phenol, cyclohexane and paraformaldehyde were added according to the molar ratio of phenolic hydroxyl group:amine group:aldehyde group of 1:1:2. After being homogeneously stirred, the mixture was heated to a molten state, reacted for 4 h and placed in a cooling unit to obtain a yellowish, translucent viscous body. The viscous body was washed, purified and dried to obtain a benzoxazine intermediate having the following structural formula, wherein the yield is 80.6%.

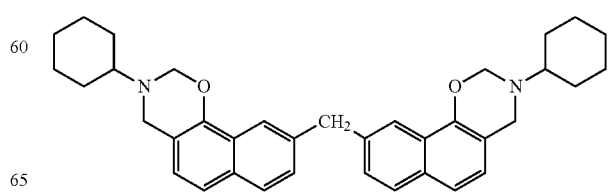

Example 6

Preparation of Benzoxazine Intermediate by the Melt Synthesis Method

At room temperature, phenol, aniline and paraformaldehyde were added according to the molar ratio of phenolic hydroxyl group:amine group:aldehyde group of 1:1:2. After being homogeneously stirred, the mixture was heated to a molten state, reacted for 4 h and placed in a cooling unit to obtain a yellowish, translucent viscous body. The viscous body was washed, purified and dried to obtain a benzoxazine intermediate having the following structural formula, wherein the yield is 73.7%.

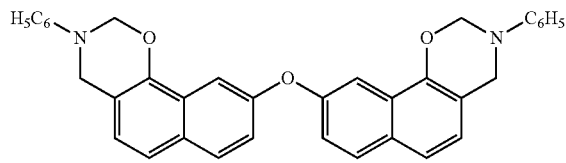

TABLE 1

| Gelation time in the examples | | | | | | |
|---|---|---|---|---|---|---|
| | Example 1 | Example 2 | Example 3 | Example 4 | Example 5 | Example 6 |
| Gelation time, 200° C. | 703 s | 656 s | 736 s | 711 s | 724 s | 627 s |

In conclusion, the benzoxazine intermediate of the present invention is prepared by using the phenol of the formula (2) as the phenol source together with primary amine and aldehyde. The benzoxazine intermediate contains a naphthalene ring structure segment, has desirable heat resistance performance and flame retarding performance and can be widely applied in composite materials. The preparation method thereof is simple and easy to operate.

Those stated above are the preferred examples of the present invention. Those ordinarily skilled in the art can make various corresponding changes and deformations according to the technical solutions and concepts of the present invention, but all said changes and deformations shall belong to the protection scope of the present invention.

The invention claimed is:

1. A benzoxazine intermediate having the structural formula (I)

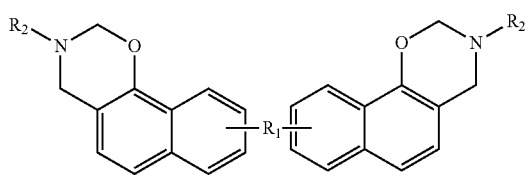

wherein $R_1$ is selected from the group consisting of O, C=O, S, $SO_2$, alicyclic hydrocarbon with 3 to 20 carbon atoms, aliphatic hydrocarbon with 1 to 20 carbon atoms, or unsaturated aliphatic hydrocarbon with 2 to 20 carbon atoms; $R_2$ is selected from the group consisting of alicyclic hydrocarbon with 3 to 20 carbon atoms, aliphatic hydrocarbon with 1 to 20 carbon atoms, or unsaturated aliphatic hydrocarbon with 2 to 20 carbon atoms.

2. A method for preparing a benzoxazine intermediate according to claim 1, comprising the following steps:

Step 1: quantifying the phenol, primary amine and aldehyde according to the molar ratio of phenolic hydroxyl group:amine group:aldehyde group of 1:(0.8-1.2):(1.5-2.5);

Step 2: mixing the phenol, primary amine and aldehyde, adding a catalyst to adjust the pH thereof to 8-10, and ending the reaction after the heating and reflux reaction for 1-8 h;

Step 3: washing with deionized water, condensing, purifying and drying the resultant solution to obtain a benzoxazine intermediate having the structural formula (I)

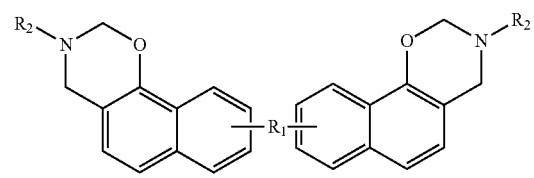

wherein $R_1$ is selected from the group consisting of O, C=O, S, $SO_2$, alicyclic hydrocarbon with 3 to 20 carbon atoms, aliphatic hydrocarbon with 1 to 20 carbon atoms, or unsaturated aliphatic hydrocarbon with 2 to 20 carbon atoms; $R_2$ is selected from the group consisting of alicyclic hydrocarbon with 3 to 20 carbon atoms, aliphatic hydrocarbon with 1 to 20 carbon atoms, or unsaturated aliphatic hydrocarbon with 2 to 20 carbon atoms.

3. The method for preparing a benzoxazine intermediate according to claim 2, wherein the catalyst is added in an amount of 0.1-5 wt. % relative to the total amount.

4. The method for preparing a benzoxazine intermediate according to claim 2, wherein the phenol has the following structural formula (2)

wherein $R_1$ is selected from the group consisting of alicyclic hydrocarbon with 3 to 20 carbon atoms, aliphatic hydrocarbon with 1 to 20 carbon atoms, or unsaturated aliphatic hydrocarbon with 2 to 20 carbon atoms.

5. The method for preparing a benzoxazine intermediate according to claim 2, wherein the primary amine is $NH_2R_2$ in which $R_2$ is selected from the group consisting of alicyclic hydrocarbon with 3 to 20 carbon atoms, aliphatic hydrocarbon with 1 to 20 carbon atoms, or unsaturated aliphatic hydrocarbon with 2 to 20 carbon atoms.

6. The method for preparing a benzoxazine intermediate according to claim 5, wherein the primary amine is selected from the group consisting of allyl amine, aniline, cyclopropylamine methylamine and ethylamine.

7. The method for preparing a benzoxazine intermediate according to claim 2, wherein the aldehyde is an aqueous formaldehyde solution or paraformaldehyde.

8. The method for preparing a benzoxazine intermediate according to claim 2, wherein the catalyst is selected from the group consisting of KOH solution, NaOH solution, ammonia, triethanolamine and triethylamine.

9. The method for preparing a benzoxazine intermediate according to claim 2, wherein the benzoxazine intermediate is prepared by the solution synthesis method or melt synthesis method, wherein, when the solution synthesis method is used, phenol, primary amine and aldehyde are added in step 2 into the solvent, heated and refluxed; the solvent is selected from the group consisting of toluene, xylene, ethanol, acetone, butanone, methylisobutanone, ethylene glycol monomethyl ether, ethylene glycol ether, ethylene glycol methyl ether acetate, methylformamide and tetrahydrofuran, or mutual compounds thereof.

* * * * *